(12) United States Patent
Fishman

(10) Patent No.: US 11,173,104 B2
(45) Date of Patent: Nov. 16, 2021

(54) NAIL POLISH FORMULATION

(71) Applicant: Yoram Fishman, Riverside, CA (US)

(72) Inventor: Yoram Fishman, Riverside, CA (US)

( * ) Notice: Subject to any disclaimer, the term of this patent is extended or adjusted under 35 U.S.C. 154(b) by 0 days.

(21) Appl. No.: 16/942,009

(22) Filed: Jul. 29, 2020

(65) Prior Publication Data

US 2020/0352846 A1 Nov. 12, 2020

Related U.S. Application Data

(63) Continuation-in-part of application No. 16/209,045, filed on Dec. 4, 2018, now abandoned, which is a continuation-in-part of application No. 15/875,290, filed on Jan. 19, 2018, now abandoned.

(51) Int. Cl.
| | |
|---|---|
| *A61K 8/81* | (2006.01) |
| *A61K 8/34* | (2006.01) |
| *A61K 8/73* | (2006.01) |
| *A61K 8/37* | (2006.01) |
| *A61Q 3/02* | (2006.01) |
| *A45D 29/00* | (2006.01) |

(52) U.S. Cl.
CPC ............ *A61K 8/8129* (2013.01); *A45D 29/00* (2013.01); *A61K 8/34* (2013.01); *A61K 8/342* (2013.01); *A61K 8/37* (2013.01); *A61K 8/731* (2013.01); *A61Q 3/02* (2013.01); *A61K 2800/43* (2013.01)

(58) Field of Classification Search
None
See application file for complete search history.

(56) References Cited

U.S. PATENT DOCUMENTS

| | | |
|---|---|---|
| 5,374,420 A | 12/1994 | Gerstein |
| 6,190,681 B1 | 2/2001 | Fishman |
| 6,254,878 B1 | 7/2001 | Bednarek et al. |
| 6,261,576 B1 | 7/2001 | Fishman |
| 6,509,009 B2 | 1/2003 | Nichols et al. |
| 2002/0197221 A1 | 12/2002 | Nichols et al. |
| 2003/0059382 A1 | 3/2003 | Brandt et al. |
| 2003/0064086 A1 | 4/2003 | Carrion et al. |
| 2009/0263338 A1 | 10/2009 | Rolland et al. |
| 2011/0136989 A1 | 6/2011 | Philbin et al. |
| 2014/0105945 A1 | 4/2014 | Bui et al. |

FOREIGN PATENT DOCUMENTS

| | | |
|---|---|---|
| WO | WO963631 | 11/1996 |

*Primary Examiner* — Danah Al-Awadi
(74) *Attorney, Agent, or Firm* — Eric Karich; Karich & Associates

(57) ABSTRACT

A composition suitable for application as a nail polish, the composition comprising: an alcohol solvent; ethylcellulose, in an amount that is about 1.0% by weight of the final composition; a film forming agent that includes maleic acid monobutyl ester-vinyl methyl ether copolymer, and maleic acid monoethyl ester-vinyl methyl ether copolymer, in an amount that is at least 40% by weight of the final composition; isostearyl alcohol, in an amount that is about 3.0% by weight of the final composition; a plasticizer in the form of a citric acid ester, in art amount that is about 1.0% by weight of the final composition; a colorant and a fragrance. This composition is suitable for application to a human nail.

1 Claim, No Drawings

NAIL POLISH FORMULATION

CROSS-REFERENCE TO RELATED APPLICATIONS

This application for a utility patent is a continuation-in-part of a previously filed utility patent application Ser. No. 16/209,045, filed Dec. 4, 2018, which claims priority to application Ser. No. 15/875,290, filed Jan. 19, 2018.

BACKGROUND OF THE INVENTION

Field of the Invention

This invention relates generally to nail polish, and more particularly to a nail polish that may be removed with alcohol.

Description of Related Art

Modern nail polish typically includes a film-forming polymer such as nitrocellulose dissolved in a volatile organic solvent such as butyl acetate. A concern for many has been that these chemicals, and also toxic chemicals which are used to remove the nail polish, can be harmful to users, and to professionals who apply the nail polish.

There is a long-felt need in the industry for a nail polish composition that avoids these health concerns by using a composition that includes an alcohol solvent. The present invention fulfills these needs and provides further advantages as described in the following summary.

SUMMARY OF THE INVENTION

The present invention teaches certain benefits in construction and use which give rise to the objectives described below.

The present invention provides a composition suitable for application as a nail polish, the composition comprising: an alcohol solvent; ethylcellulose, in an amount that is about 1.0% by weight of the final composition; a film forming agent that includes maleic acid monobutyl ester-vinyl methyl ether copolymer, and maleic acid monoethyl ester-vinyl methyl ether copolymer, in an amount that is at least 40% by weight of the final composition; isostearyl alcohol, in an amount that is about 3.0% by weight of the final composition; a plasticizer in the form of a citric acid ester, in an amount that is about 1.0% by weight of the final composition; a colorant; and a fragrance. This composition is suitable for application to a human nail.

A primary objective of the present invention is to provide a nail polish composition having advantages not taught by the prior art.

Another objective is to provide a nail polish composition that has superior nail polish characteristics.

Another objective is to provide a nail polish composition that does not include harsh and toxic chemicals which are harmful to a human or other animal that has the composition applied to its nails.

Another objective is to provide a nail polish composition that may be removed with alcohol, without the use of harsh and toxic chemicals.

A further objective is to provide a nail polish composition that does not have an offensive chemical smell, but which may include a fragrance so that the composition has an attractive smell.

Other features and advantages of the present invention will become apparent from the following more detailed description which illustrate, by way of example, the principles of the invention.

DETAILED DESCRIPTION OF THE INVENTION

The above-described drawing figures illustrate the invention, a composition suitable for application as a nail polish. The composition comprises ingredients that are not harmful to the person's nails and health, and furthermore the composition may be removed with alcohol rather than more toxic chemicals typically used.

The composition includes an alcohol solvent. By providing the composition with an alcohol solvent as its base, the nail polish may be removed with alcohol rather than acetone or other powerful and damaging chemical. In this embodiment, the alcohol includes ethyl alcohol, and includes effective amounts of denaturing ingredients, for consumer safety. For purposes of this application, the term "effective amount" is defined to mean an amount deemed suitable by one skilled in the art for achieving the desired goal, in this case to prevent consumption of the alcohol. In the present embodiment, the specially denatured (SD) ethyl alcohol is specially denatured alcohol (SDA) 40-B 200 Proof. This includes denatonium benzoate as the denaturing ingredient. In this embodiment, to every 100 gallons of ethyl alcohol, 1/16 avoirdupois ounce of denatonium benzoate, NF, is added, along with 1/8 gallon of tert-butyl alcohol.

The composition includes a cellulose polymer material and an acrylic co-polymer material, both of which are soluble in alcohol. In this embodiment, the cellulose polymer material is an ethylcellulose polymer material, such as ETHOCEL®, which is sold by Dow Chemical.

In another embodiment, the cellulose polymer material is hydroxypropyrl cellulose, or hydroxyethyl cellulose.

The composition further includes isostearyl alcohol, a plasticizer and a colorant. The isostearyl alcohol and the plasticizer are carefully selected and provided in an amount that results in the composition being stable, having a viscosity that is suitable for application as a nail polish, and that will dry in less than 5 minutes. In this embodiment, the plasticizer is a citric acid ester such as CIRTOFLEX® 2, which is sold by Vertellus Corporation. In another embodiment, the plasticizer includes Tributyl Citrate, Acetyl Triethyl Citrate, Acetyl Tributyl Citrate, Acetyl Trihexyl Citrate, or an equivalent material.

Prior to use, the composition should be liquid that is thin and viscous enough to be easily be spread on the nails of a person in a thickness that is deemed appropriate to consumers and to those skilled in the art, while also having a fast enough drying time to be deemed acceptable to consumers and to those skilled in the art. The composition is deemed "dry" when it is no longer damaged or transferred to other surfaces through gentle contact.

Extensive experimentation has determined a composition suitable for application as a nail polish, the composition comprising:
alcohol solvent 50.0-95.0% by weight;
ethocellulose polymer material 1.0-5.0% by weight;
an acrylic co-polymer material (film forming agent) at least 60%, by weight;
isostearyl alcohol 2.0-8.0% by weight;
a plasticizer 0.25-10.0% by weight;
a fragrance; and
a colorant.

In a preferred embodiment, the composition includes the following (all percentages by final weight):
- alcohol solvent;
- ethylcellulose, about 1.0%;
- film forming agent that includes maleic acid monobutyl ester-vinyl methyl ether copolymer, and maleic acid monoethvl ester-vinyl methyl ether copolymer, at least 40.0%, and in one embodiment 60-65%;
- isostearyl alcohol, about 3.0%;
- plasticizer citric acid ester, about 1.0%;
- colorant, about 1.0-1.5%; and
- fragrance, about 0.50%.

The film forming agent may include copolymers of monoalkyl esters of poly (methyl vinyl ether/maleic acid) with varying ester groups, preferably the product sold under the trademark Gantrez™ (A-425).

In this embodiment, the composition further includes about 0.5% of an alcohol-soluble fragrance, such as an alcohol-soluble fragrance oil, or other suitable fragrance known in the art. In one embodiment, the fragrance is an oil sold by Gorgio®, type CP00264. Obviously, one skilled in the art may adjust the quantities of these ingredients, and he or she may substitute the ingredients with equivalent materials, according to the practices of those skilled in the art, and these equivalent formulations should be considered within the scope of the present invention.

The invention further includes a unique method of producing the nail polish composition using a unique series of heating and cooling while mixing the components, to provide superior results. The method includes the first step of heating the alcohol solvent to about 110 degrees Fahrenheit, and adding the ethylcellulose, in an amount that is about 1.0% by weight of the final composition, to the alcohol solvent.

Importantly, the combination of the alcohol solvent and the ethylcellulose is heated to at least 150 degrees Fahrenheit preferably about 155 degrees. The film forming agent is then added in an amount that is at least 40% by weight of the final composition, to the alcohol solvent and ethylcellulose. The film forming agent comprising maleic acid monobutyl ester-vinyl methyl ether copolymer, and maleic acid monoethyl ester-vinyl methyl ether copolymer. This forms a first mixture, and it is allowed to cool to about 100 degrees Fahrenheit.

A second'mixture is formed by combining isostearyl alcohol, in an amount that is about 3.0% by weight of the final composition, a plasticizer in the form of a citric acid ester, in an amount that is about 1.0% by weight of the final composition, a colorant, and a fragrance. The second mixture is heated to about 110 degrees Fahrenheit, and then the first and second mixtures are combined while thoroughly mixing. The resulting nail polish composition is then allowed to cool to room temperature, at which time it may be packaged in a manner known in the art. This cooled composition is then applied to the human nail.

While generally similar compositions (lacking the plasticizer) are applied to the skin (e.g., lips), this type of composition, with the high level of film forming agent, and not generally considered suitable for application to a nail, because it was not typically thought to be durable enough to be suitable for use as a nail polish. However, this particular combination, including the plasticizer, and the high level of film forming agent, has been found by much experimentation to be suitable for use as a nail polish, it provides a suitable shine, remains bright for a suitable period of time, and resists cracking on the nail through the drying process.

Nichols, U.S. 2002/0197221, teaches a composition suitable for use on lips, not on nails. Furthermore, this reference does not teach the use of a plasticizer, as this is not necessary on lips, but is essential for use on nails. Furthermore, while Nichols teaches a film forming agent preferable in the amount of 6% (although a maximum of 50% is mentioned, this is not enabled, and at no point is 60% considered, and is certainly contrary to the 6% disclosed as preferred).

As used in this application, the words "a," "an," and "one" are defined to include one or more of the referenced item unless specifically stated otherwise. The terms "approximately" and "about" are defined to mean +/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is, not limited to these embodiments, but rather the scope of the invention is defined by the following claims.

What is claimed is:

1. A method for coloring a human nail, the method comprising the steps of:
   producing a nail polish composition using the following steps:
      providing an alcohol solvent;
      heating the alcohol solvent to about 110 degrees Fahrenheit;
      adding ethylcellulose, in an amount that is about 1.0% by weight of the final composition, to the alcohol solvent;
      heating the combination of the alcohol solvent and the ethylcellulose to at least 150 degrees Fahrenheit;
      adding a film forming agent, in an amount that is at least 40% by weight of the final composition, to the alcohol solvent and ethylcellulose, the film forming agent comprising maleic acid monobutyl ester-vinyl methyl ether copolymer, and maleic acid monoethyl ester-vinyl methyl ether copolymer, to form a first mixture;
      cooling the first mixture to about 100 degrees Fahrenheit;
      forming a second mixture by combining isostearyl alcohol, in an amount that is about 3.0% by weight of the final composition, a plasticizer in the form of a citric acid ester, in an amount that is about 1.0% by weight of the final composition, a colorant, and a fragrance;
      heating the second mixture to about 110 degrees Fahrenheit;
      combining the first and second mixtures while thoroughly mixing; and
      allowing the nail polish composition to cool to room temperature; and
   applying the composition to the human nail.

* * * * *